US012733964B2

(12) United States Patent
Martinez Ferro et al.

(10) Patent No.: US 12,733,964 B2
(45) **Date of Patent: *Sep. 15, 2026**

(54) U-BLOG CHEST WALL SYSTEM

(71) Applicant: PAMPAMED SRL, Buenos Aires (AR)

(72) Inventors: Marcelo Hernan Martinez Ferro, Olivos (AR); Gaston Bellia-Munzon, Buenos Aires (AR)

(73) Assignee: PAMPAMED SRL, Buenos Aires (AR)

( * ) Notice: Subject to any disclaimer, the term of this patent is extended or adjusted under 35 U.S.C. 154(b) by 0 days.

This patent is subject to a terminal disclaimer.

(21) Appl. No.: 19/080,624

(22) Filed: Mar. 14, 2025

(65) Prior Publication Data

US 2025/0204965 A1 Jun. 26, 2025

Related U.S. Application Data

(63) Continuation-in-part of application No. 17/045,681, filed as application No. PCT/EP2019/058924 on Apr. 9, 2019, now Pat. No. 12,279,797.

(60) Provisional application No. 62/699,486, filed on Jul. 17, 2018, provisional application No. 62/655,532, filed on Apr. 10, 2018.

(51) Int. Cl.
*A61B 17/80* (2006.01)
*A61B 17/88* (2006.01)

(52) U.S. Cl.
CPC ........ *A61B 17/8076* (2013.01); *A61B 17/808* (2013.01); *A61B 17/8872* (2013.01)

(58) Field of Classification Search
CPC ..... A61B 17/82; A61B 17/823; A61B 17/842; A61B 17/844; A61B 2017/681
See application file for complete search history.

(56) References Cited

U.S. PATENT DOCUMENTS

| | | | | |
|---|---|---|---|---|
| 6,682,532 | B2 * | 1/2004 | Johnson | A61B 17/7007 606/279 |
| 7,156,847 | B2 * | 1/2007 | Abramson | A61B 17/8076 606/71 |
| 8,308,761 | B2 * | 11/2012 | Brailovski | A61B 17/06166 606/228 |
| 10,357,236 | B2 * | 7/2019 | De Mayo | A61B 17/025 |
| 10,383,614 | B2 * | 8/2019 | Larson | A61B 17/025 |
| 11,786,273 | B2 * | 10/2023 | Roger | A61B 17/7043 606/253 |
| 2004/0127906 | A1 * | 7/2004 | Culbert | A61B 17/70 606/279 |

* cited by examiner

*Primary Examiner* — Anu Ramana
(74) *Attorney, Agent, or Firm* — LUMEN PATENT FIRM

(57) ABSTRACT

A flail chest stabilization device is provided that includes a pair of lateral bridges, a pair of main stabilization bars, a screw/fastener and slider-element connector assembly, and a slider introducer tool, where the slider introducer tool positions the slider-element, where the main stabilization bars are connected by the screw/fastener and slider connector assembly to the lateral bridges, where the stabilization bars are in a parallel configuration or crossed configuration.

11 Claims, 20 Drawing Sheets

100
300
104
104
102
106A
106B 106
104
300
104

102
300
104
106
104
102
106

100
400
106
102
104
102
104
106

400
104
106
102
104
106
102

400
102
106
102

U-BLOG CHEST WALL SYSTEM

CROSS-REFERENCE TO RELATED APPLICATIONS

This application is a continuation-in-part of U.S. patent application Ser. No. 17/045,681 filed Oct. 6, 2020, now U.S. Pat. No. 12,279,797 issued Apr. 22, 2025, which is incorporated herein by reference. U.S. patent application Ser. No. 17/045,681 is a 371 of PCT/EP2019/058924 filed Apr. 9, 2019. PCT/EP2019/058924 claims the benefit of U.S. Provisional application 62/655,532 filed Apr. 10, 2018. PCT/EP2019/058924 claims the benefit of U.S. Provisional application 62/699,486 filed Jul. 17, 2018.

FIELD OF THE INVENTION

The present invention relates generally to surgical stabilization of flail chest, chest wall bone fractures after trauma and/or the correction of chest wall deformities. More particularly, the invention relates to severe chest wall trauma and complex deformities of the anterior chest wall that need to be stabilized and/or corrected surgically by means of chest wall remodeling and surgical stabilization.

BACKGROUND OF THE INVENTION

Flail chest is a life-threatening medical condition that occurs when a segment of the rib cage breaks due to trauma and becomes detached from the rest of the chest wall.

What is needed is a flail chest stabilization device that implants to a patient's body without connecting to a muscle, a rib or any surrounding tissue.

SUMMARY OF THE INVENTION

To address the needs in the art, a flail chest stabilization device is provided that includes a pair of lateral bridges, a pair of main stabilization bars, a screw/fastener and slider-element connector assembly, and a slider introducer tool, where the slider introducer tool positions the slider-element, where the main stabilization bars are connected by the screw/fastener and slider connector assembly to the lateral bridges, where the stabilization bars are in a parallel configuration or crossed configuration.

According to one aspect of the invention, the main stabilization bar is thicker in a center region relative to each end region, where the thicker center region imparts a central stabilization force that is greater than an end stabilization force.

In another aspect of the invention, the main stabilization bar includes a T-shape slot or a linear shape slot at each end. In one aspect, the slider-element further includes a spoiler block configured to limit a range of travel for the slider-element within the stabilization bar T-shape slot, where the screw/fastener and slider element assembly are moveably engaged with the T-shape slot or the linear shape slot.

In a further aspect, the invention includes a middle stabilization bar connected to the lateral bridges, where the middle stabilization bar is configured to provide antero-posterior stabilization. In one aspect, the middle stabilization bar includes a single thickness from end to end, where the middle stabilization bar has a plurality multiple threaded holes, or slots on each the end. In a further aspect, the middle stabilization bar is configured to impart a force that goes from front to back of a rib cage, where the imparted force flattens asymmetric deformities or stabilizes fractured bones. In another aspect, the middle bar is connected to the lateral bridges by lateral secondary mini-bridges (or aka as brackets), where the lateral secondary mini-bridges (or brackets) are connected to the lateral bridges by the screw/fastener and slider-element connector assembly, where the middle stabilization bar is connected to the secondary mini-bridge by a threaded screw or a fastener.

In yet another aspect of the invention, the flail chest stabilization device implants to a patient's body without connecting to a muscle, a rib or any surrounding tissue.

According to one aspect of the invention, the lateral bridges include a flat or curved profile. In one aspect, the invention further includes a superior parallel stabilization bar, where the main stabilization bars are connected to the curved lateral in the crossed configuration, where the superior parallel stabilizer bar is connected to the flat lateral bridges, where the flat lateral bridges are further connected to the main stabilization bars.

According to another aspect of the invention, the slider introducer tool is positioned under the main stabilization bar during a surgical procedure.

DETAILED DESCRIPTION

The current invention is a device for the stabilization of flail chest, including multiple chest wall bone fractures and/or the correction of deformities of the anterior chest wall.

The system according to the current invention is different because it avoids fixation of the implants to the patient's body parts (muscles, ribs and surrounding tissues) as the system fixates by its own. The fixation method is original (sliders, bridges, fasteners and/or screws). Also, the possibility of crossed main stabilization bars with original curved bridges are innovative. The crossed stabilization bars can be combined to a superior parallel stabilization bars, thus the fixation system requires a combined curved-straight bridges.

This is a system comprised of main stabilization bars that can be parallel or crossed and are fixed laterally by bridges.

The main stabilization bar is thicker in the center where mayor forces are required and thinner in both ends where less stabilization forces are required.

There are two models of main stabilization bars, with (T shape slot) or without horizontal slot depending on the model of slider to be used.

The main lateral bridges are fixed by means of sliders and screws/fasteners. There are two model of sliders, with and without spoiler. The slider with spoiler is intended to be used with the main stabilization bar that has T shaped slots.

In certain complex thoracic deformities or extremely severe chest trauma with sternal fractures that need mixed stabilization forces (anterior and posterior forces) a novel three bars system in which the middle bar and the lateral bridges provide combined antero-posterior stabilization has been designed.

In this specific variant, the middle bar has the same thickness from end to end and has a fixation method comprised of multiple threaded holes on each end. This middle bar is used to apply a force that goes from front to back in order to flatten asymmetric deformities or stabilize fractured bones such as the sternum. In order to fix this middle bar, two lateral secondary mini-bridges are fixed to the middle bar by means of one or two screws/fasteners. Screws/fasteners are placed into the threaded holes located at the end of the middle bar. The main bridges are used as an anchor for the middle bar fixation by means of the secondary mini-bridges.

Special original and innovative instrumentation has been designed for the delivery and placement of the sliders called "sliders introducers" that need to be placed under the main stabilization bar during the surgical procedure.

Figures 1A, 1B, 1C, 1D, 1E:
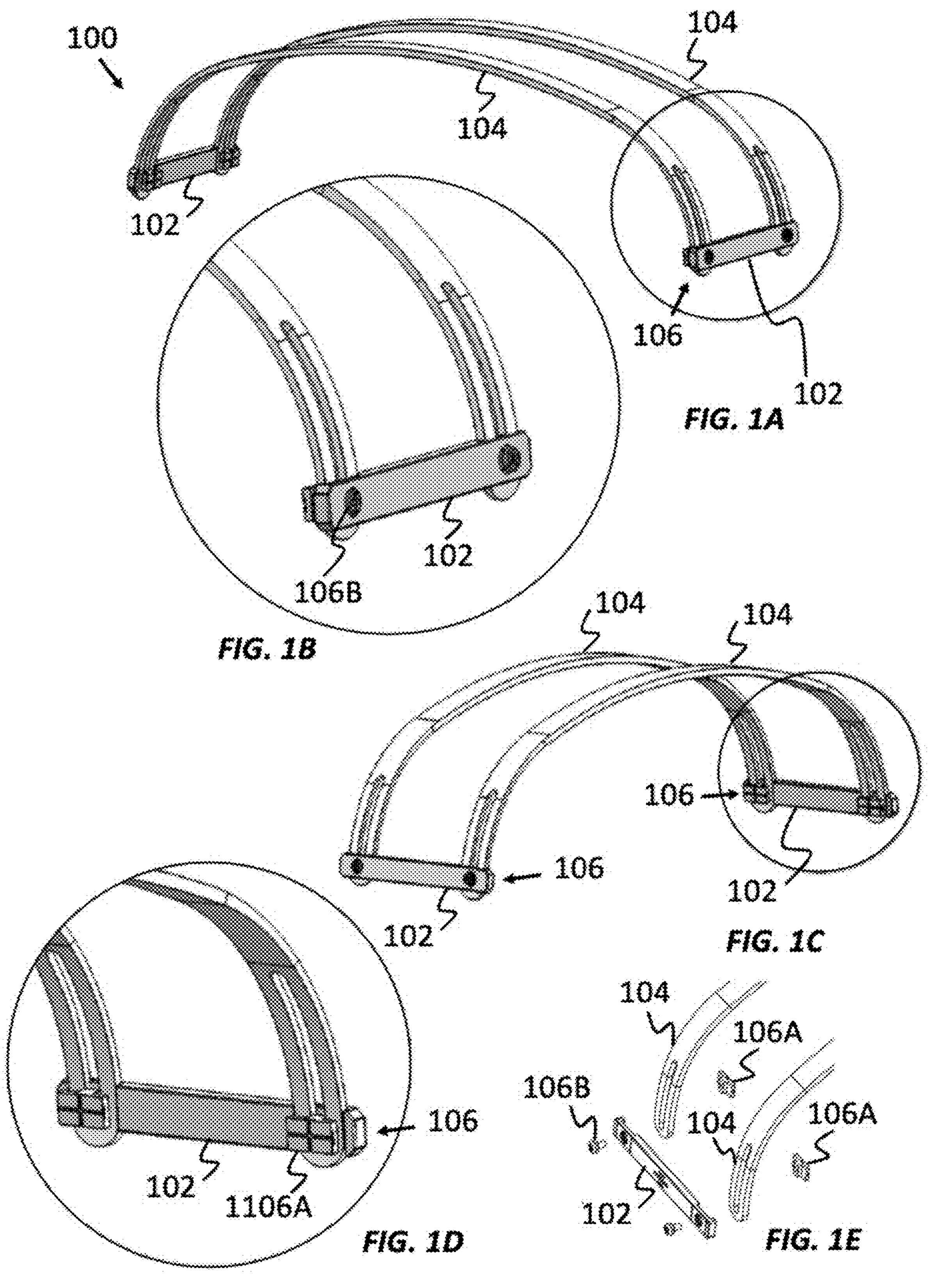
FIGS. 1A-1G show one embodiment of a flail chest stabilization device.
Figure 1F:
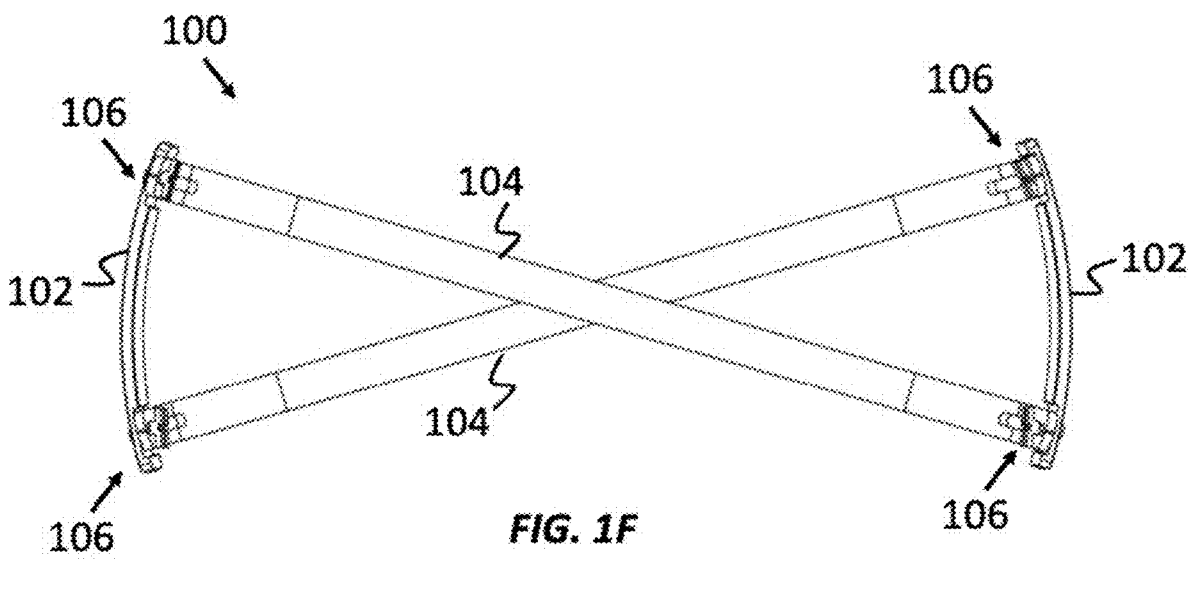

Turning now to the figures, one embodiment of a flail chest stabilization device 100 is provided in FIGS. 1A-1G, that includes a pair of lateral bridges 102, a pair of main stabilization bars 104, a screw/fastener and slider-element connector assembly 106, and a slider introducer tool 108, where the slider introducer tool 108 positions the slider-element 106A, where the main stabilization bars 102 are connected by the screw/fastener 106B and slider connector 106A assembly 106 to the lateral bridges 102, where the stabilization bars 104 are in a parallel configuration or crossed configuration (see FIG. 1F). As shown, lateral bridges 102 include a flat or curved profile.

Figure 1G:
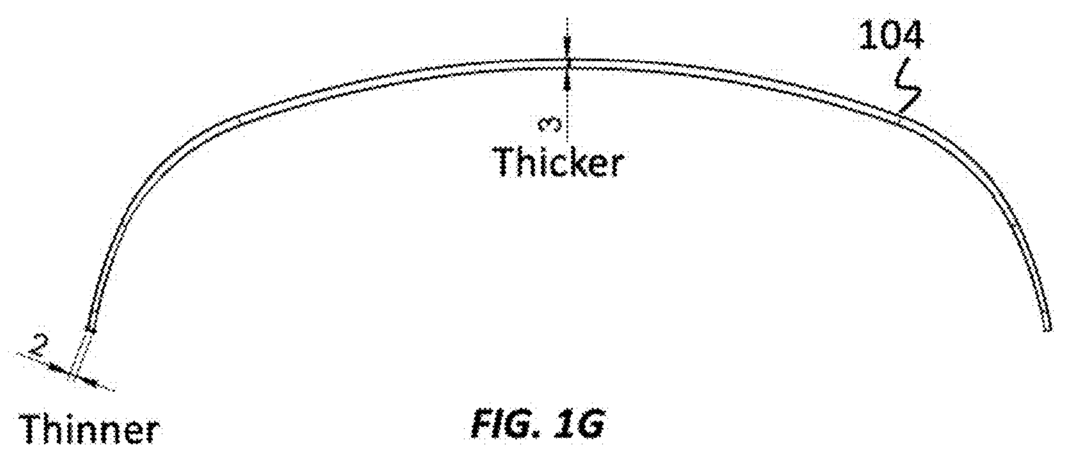
Figures 2A, 2B, 2C, 2D, 2E, 2F:
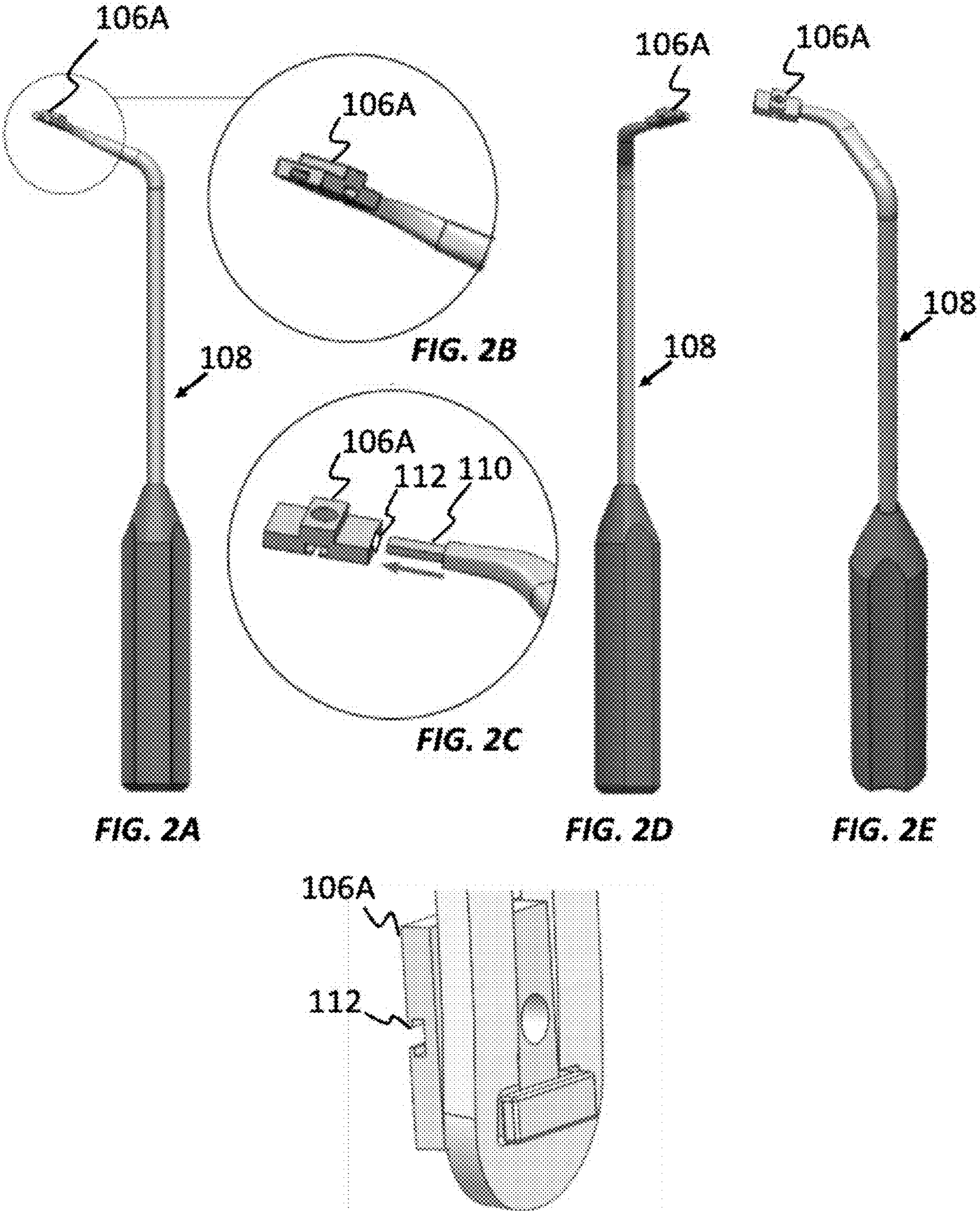
FIGS. 2A-2F show how the slider introducer tool engages the slider-element by inserting an introducer tip into a slider-element port, according to one embodiment of the invention.

FIG. 1G shows the main stabilization bar 104 is thicker in a center region relative to each end region, where the thicker center region imparts a central stabilization force that is greater than an end stabilization force.

According to another aspect of the invention, the slider introducer tool 108 is positioned under the main stabilization bar 104 during a surgical procedure, where there are two different model of slider introducers, a left-handed and a right-handed. The slider introducer tool engages the slider-element 106A by inserting an introducer tip 110 into a slider-element port 112, as shown in FIGS. 2A-2E.

Figures 3A, 3B, 3C, 3D:
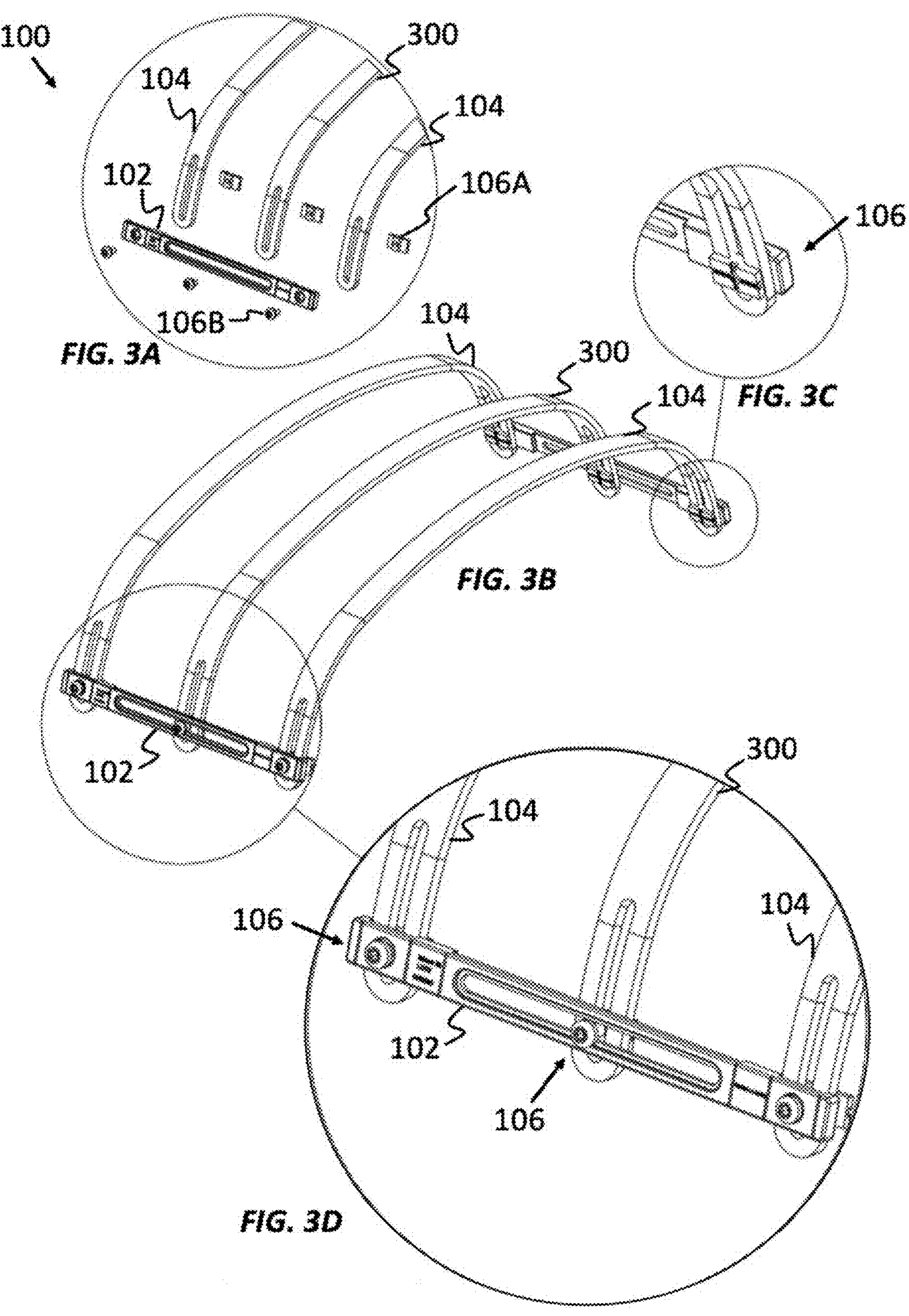
FIGS. 3A-3S show a middle stabilization bar connected to the lateral bridges, where the middle stabilization bar is configured to provide antero-posterior stabilization, where (3P-3S) show an assembled structure with a representative implementation, according to one embodiment of the invention.
Figures 3E, 3F, 3G:
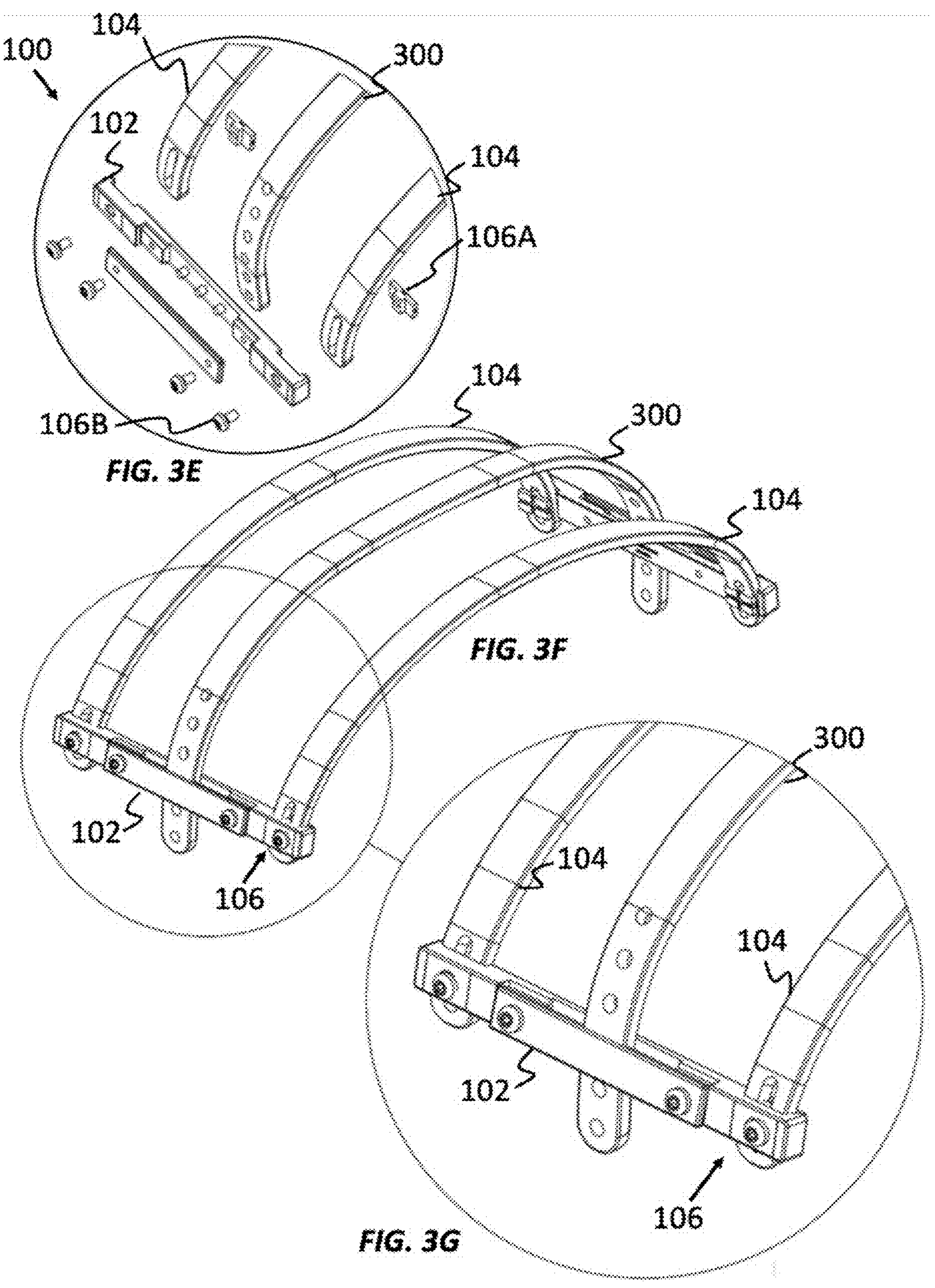
Figures 3H, 3I, 3J, 3K:
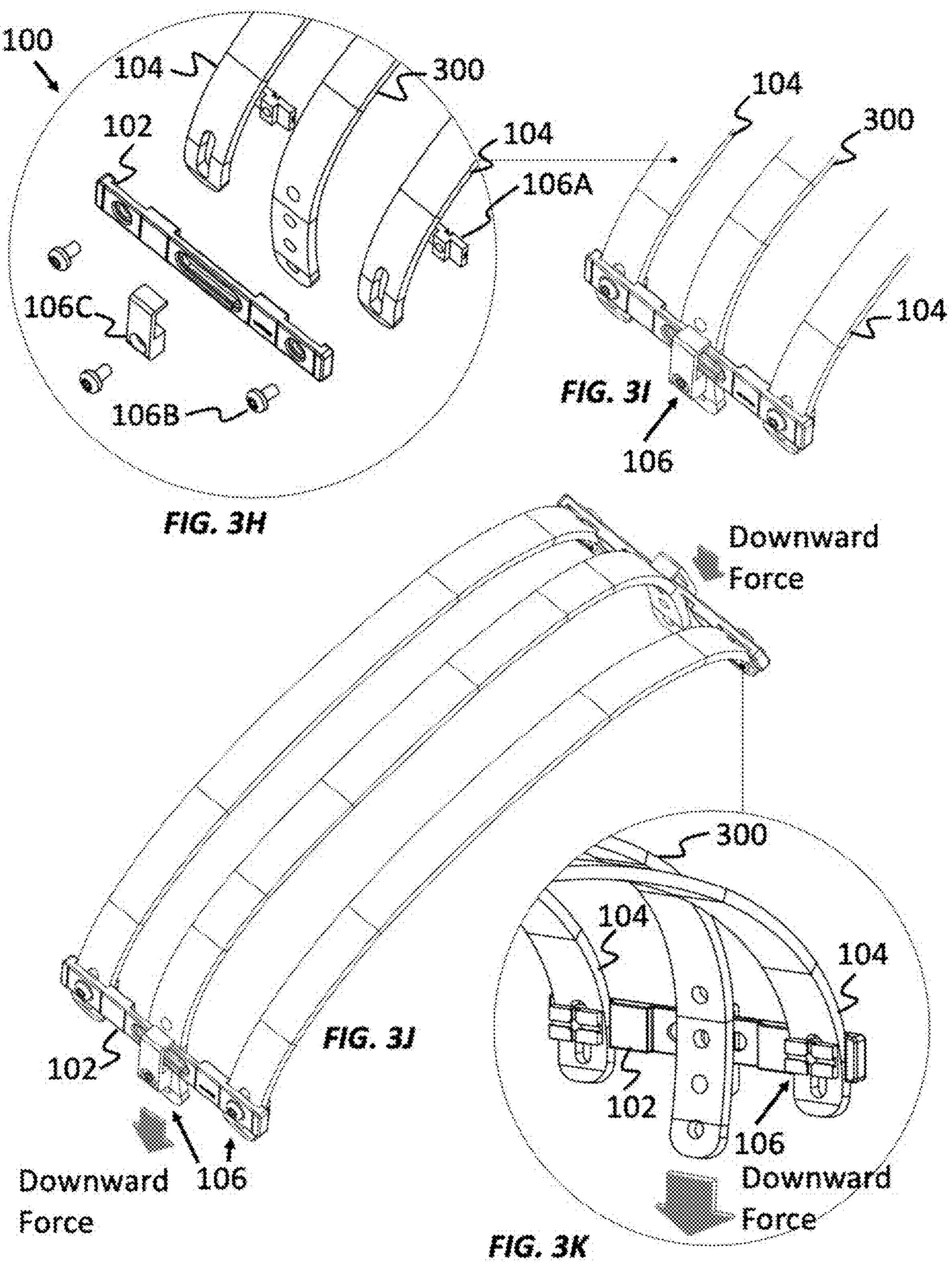
Figures 3L, 3M, 3N, 3O:
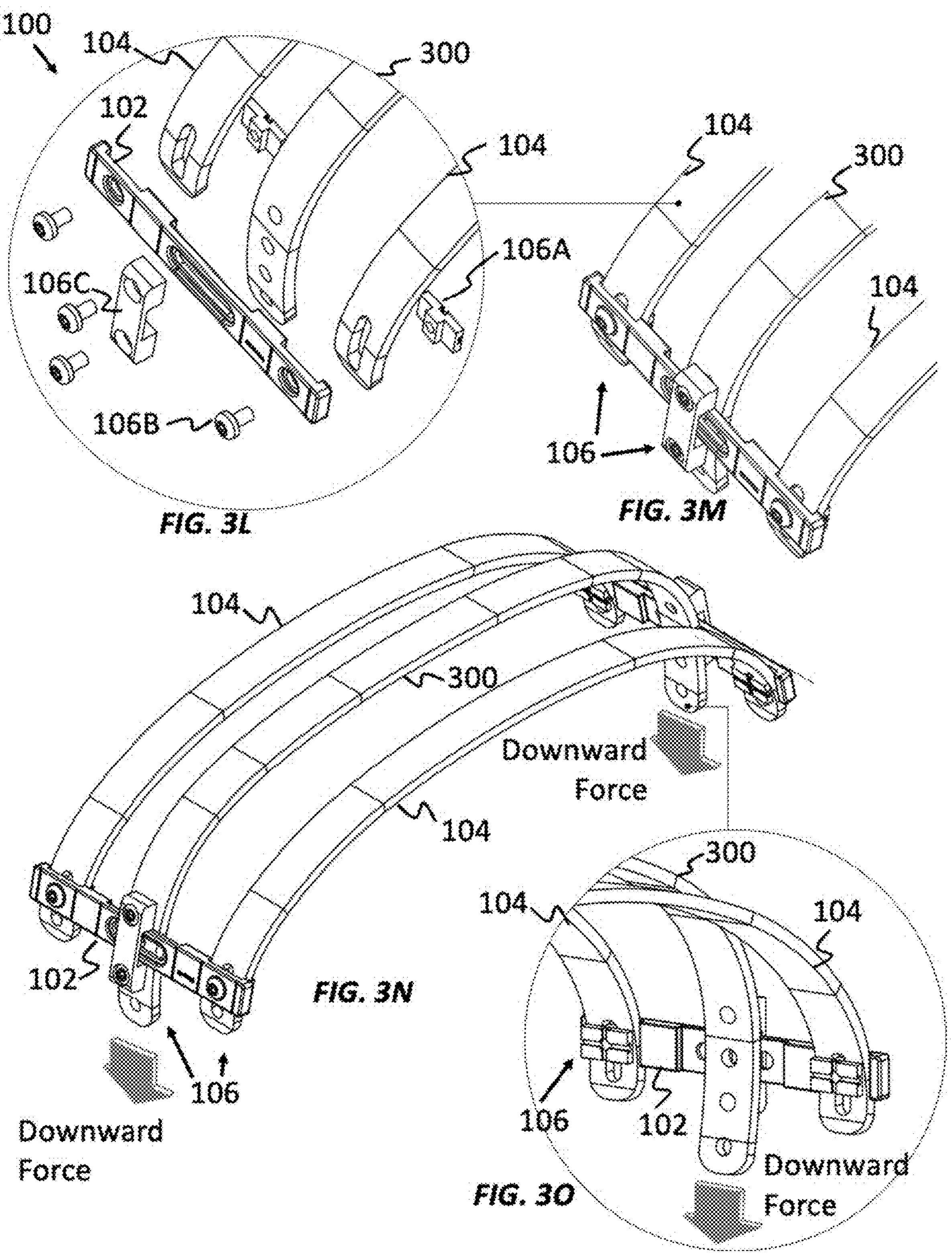
Figure 3P:
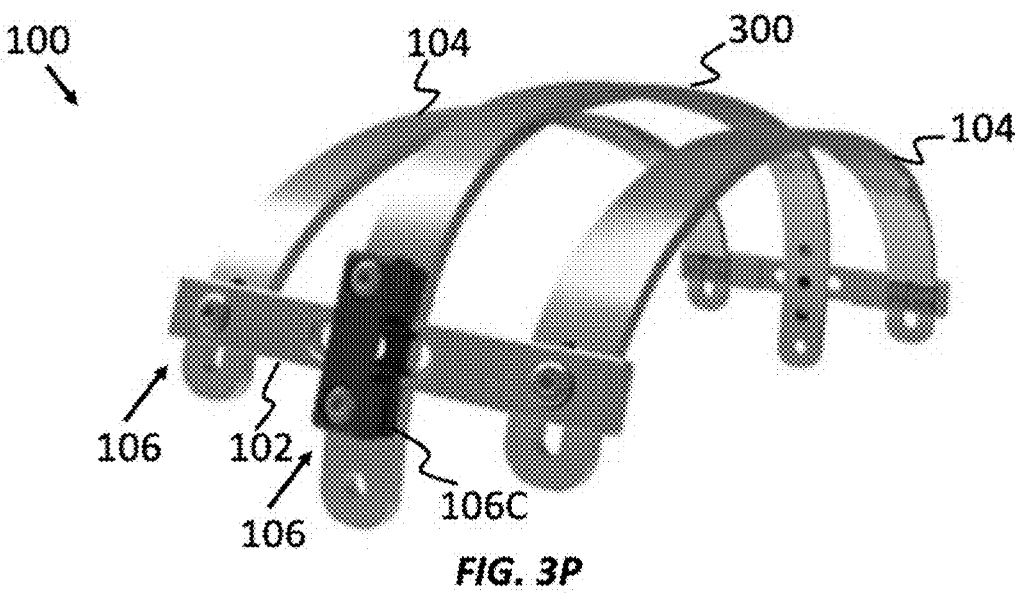
Figure 3Q:
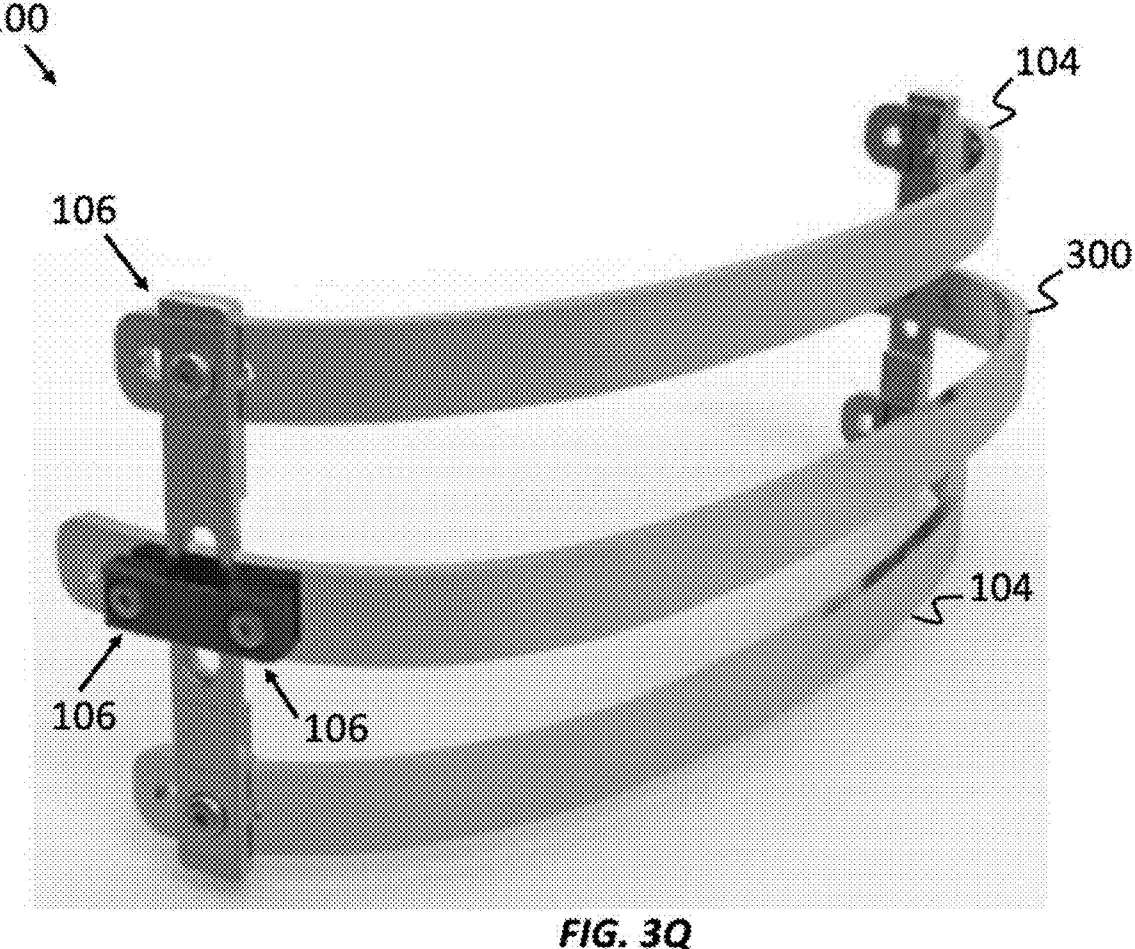
Figure 3R:
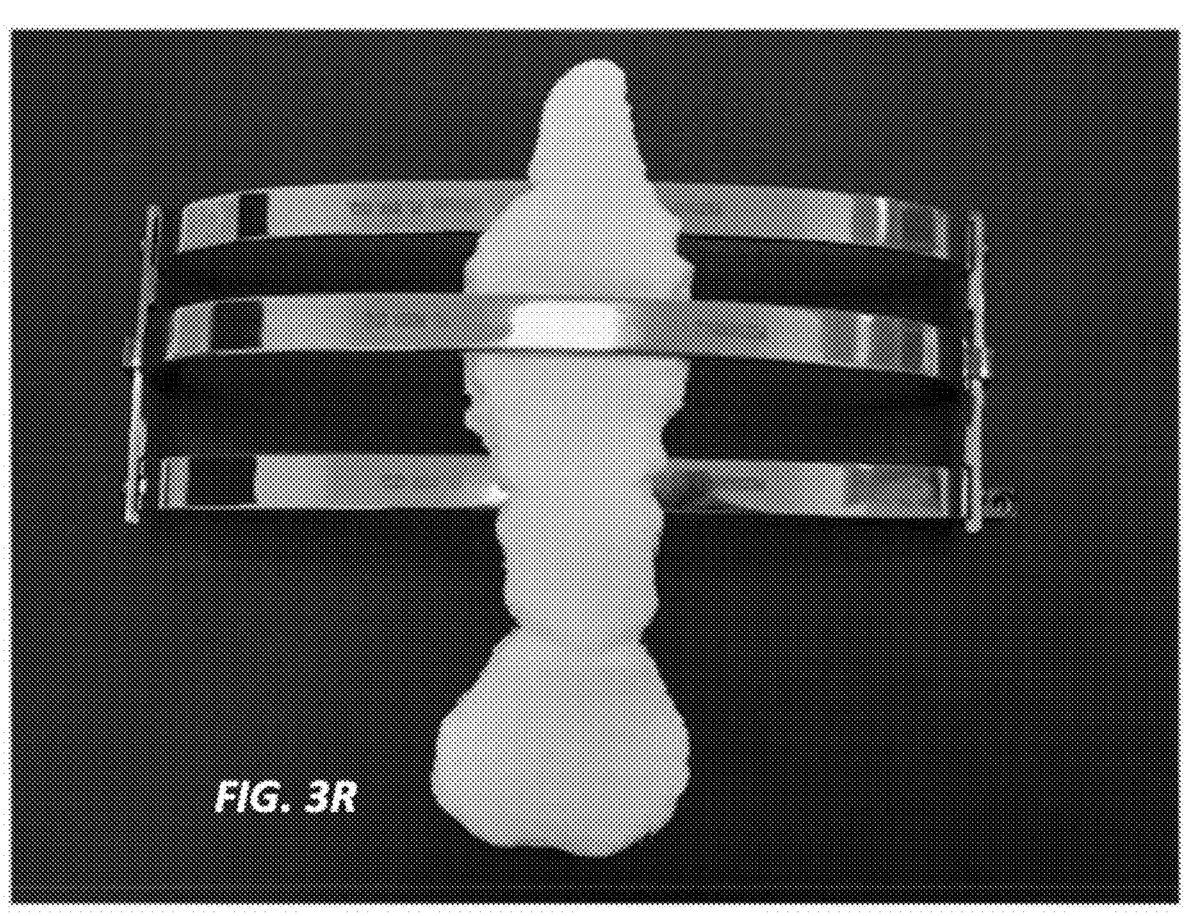
Figure 3S:
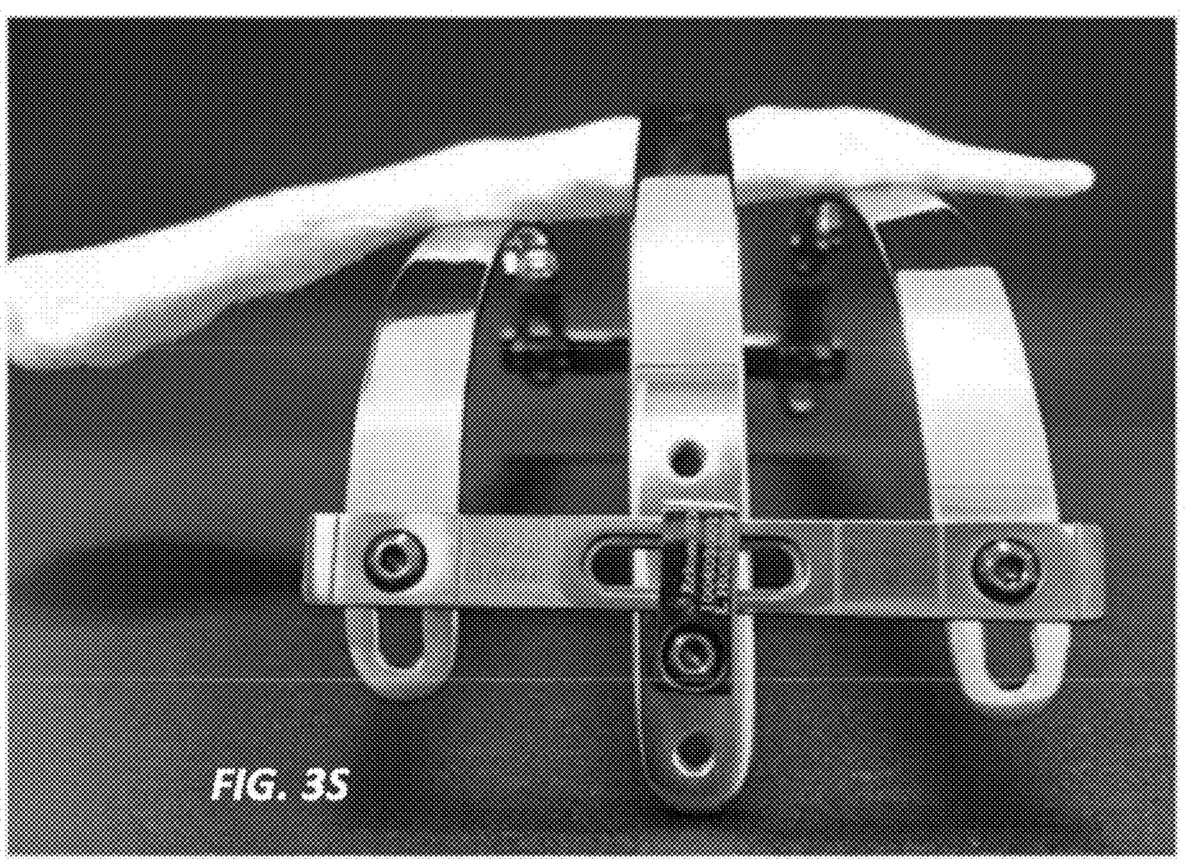

FIGS. 3A-3S show further embodiments, where the invention includes a middle stabilization bar 300 connected to the lateral bridges 102, where the middle stabilization bar 300 is configured to provide antero-posterior stabilization. In one aspect, the middle stabilization bar includes a single thickness from end to end, where the middle stabilization bar has a plurality multiple threaded holes, or slots on each end. In a further aspect, the middle stabilization bar is configured to impart a force that goes from front to back of a rib cage, where the imparted force flattens asymmetric deformities or stabilizes fractured bones. In another aspect, the middle bar is connected to the lateral bridges by lateral secondary mini-bridges 106C, where the lateral secondary mini-bridges 106C are connected to the lateral bridges 102 by the screw/fastener and slider-element connector assembly 106, where the middle stabilization bar 300 is connected to the secondary mini-bridge 106C by a threaded screw or fastener. In the embodiments shown in FIGS. 3H-3S, the middle stabilization bar 300 is connected to the lateral bridges 102 using a mini-bridge or bracket 106C, where the middle stabilization bar is disposed to exert a downward force on the chest, relative to the other main stabilization bars 104.

Figures 4A, 4B, 4C:
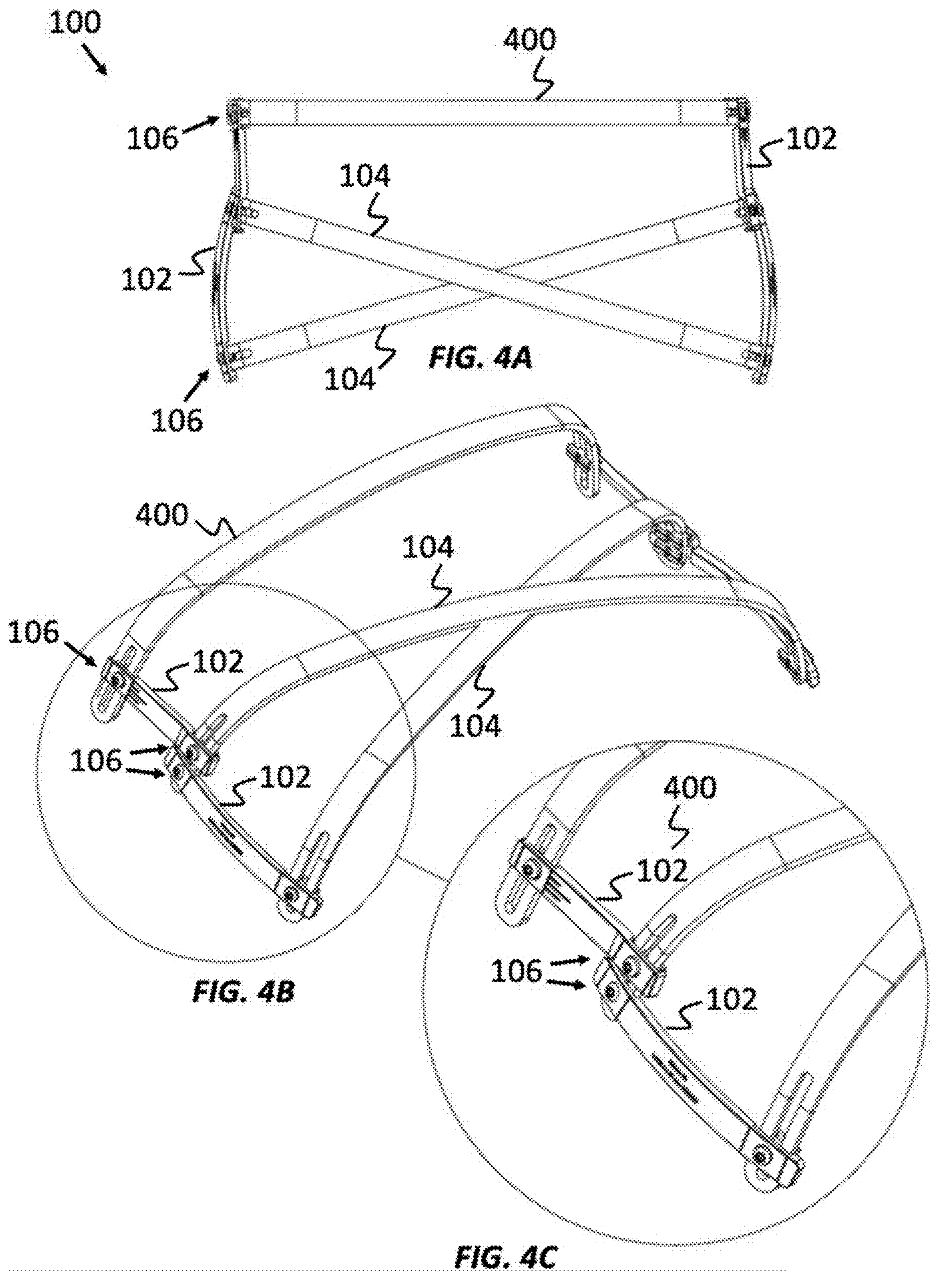
FIGS. 4A-4C show a superior parallel stabilization bar are connected to the curved lateral bridges in the crossed configuration, according to the current invention.

In a further embodiment, FIGS. 4A-4C show the invention further includes a superior parallel stabilization bar 400, where the main stabilization bars 103 are connected to the curved lateral bridges 102 in the crossed configuration, where the superior parallel stabilizer bar is connected to the flat lateral bridges 102, where the flat lateral bridges 102 are further connected to the main stabilization bars 104.

Figure 5A:
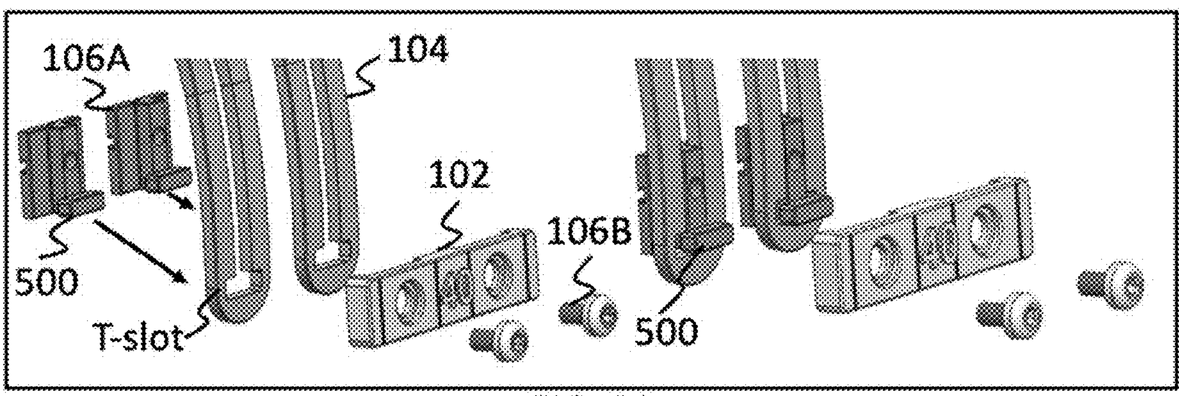
FIGS. 5A-5O show the main stabilization bar includes a T-shape slot with the slider-element further having a spoiler block configured to limit a range of travel for the slider-element within the stabilization bar T-shape slot, according to the current invention.
Figure 5B:
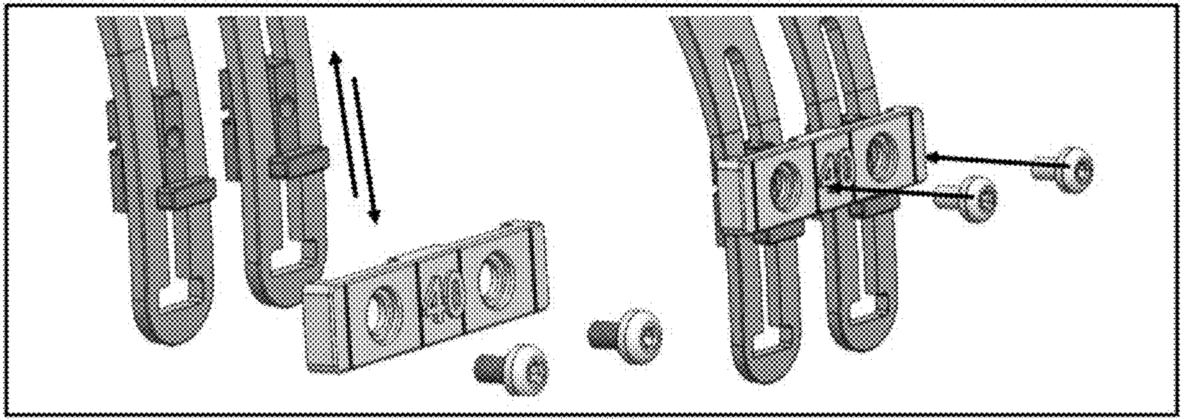
Figure 5C:
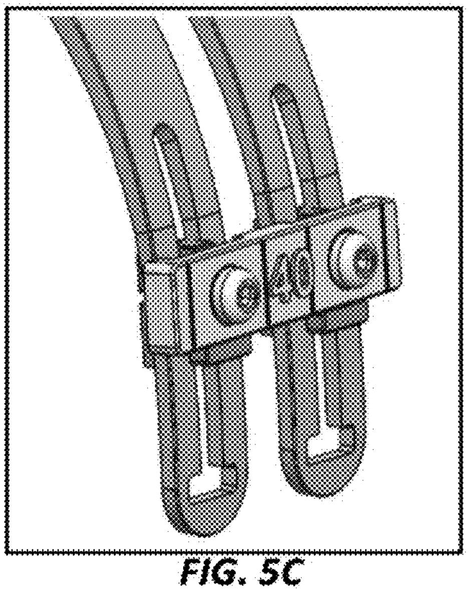
Figure 5D:
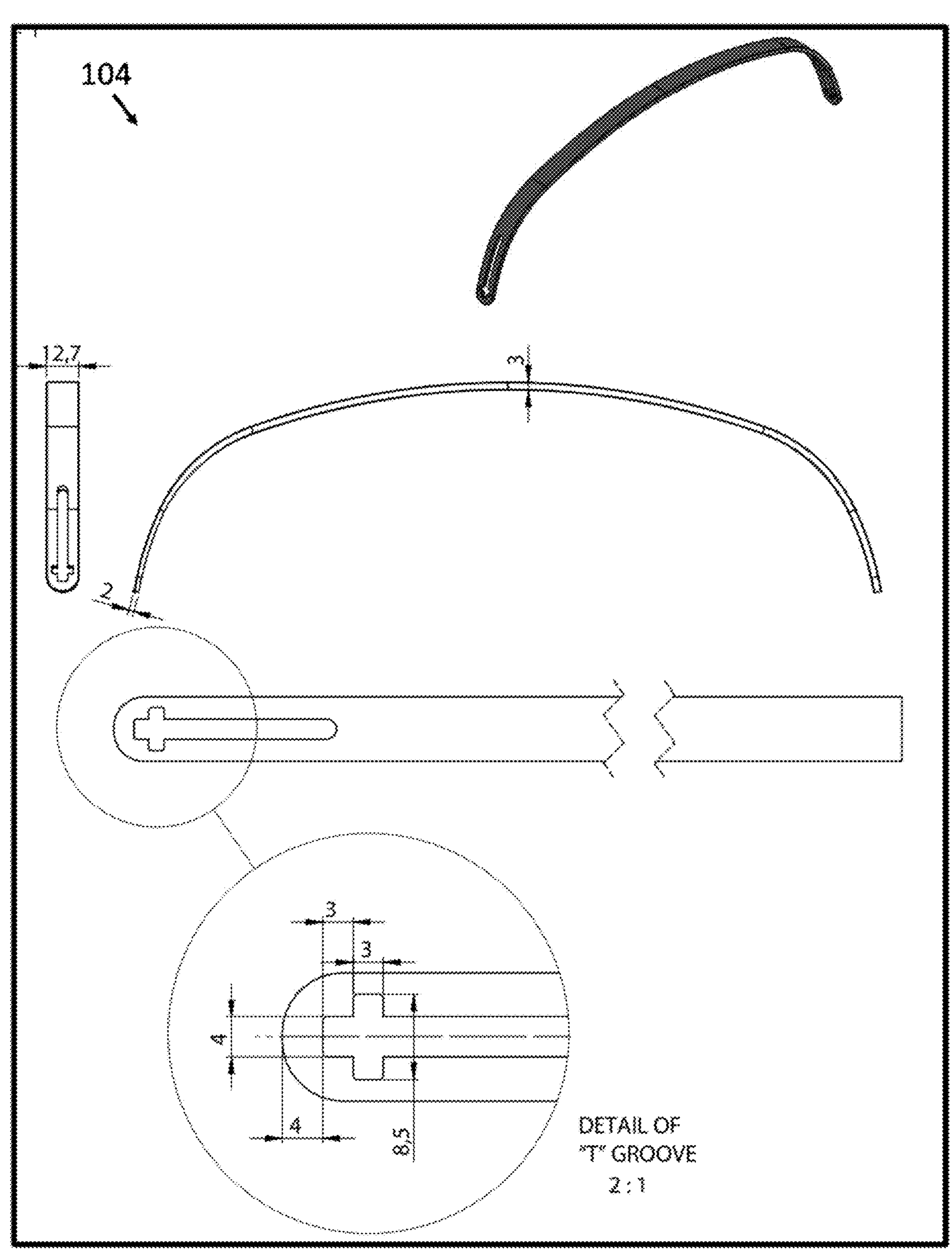
Figure 5E:
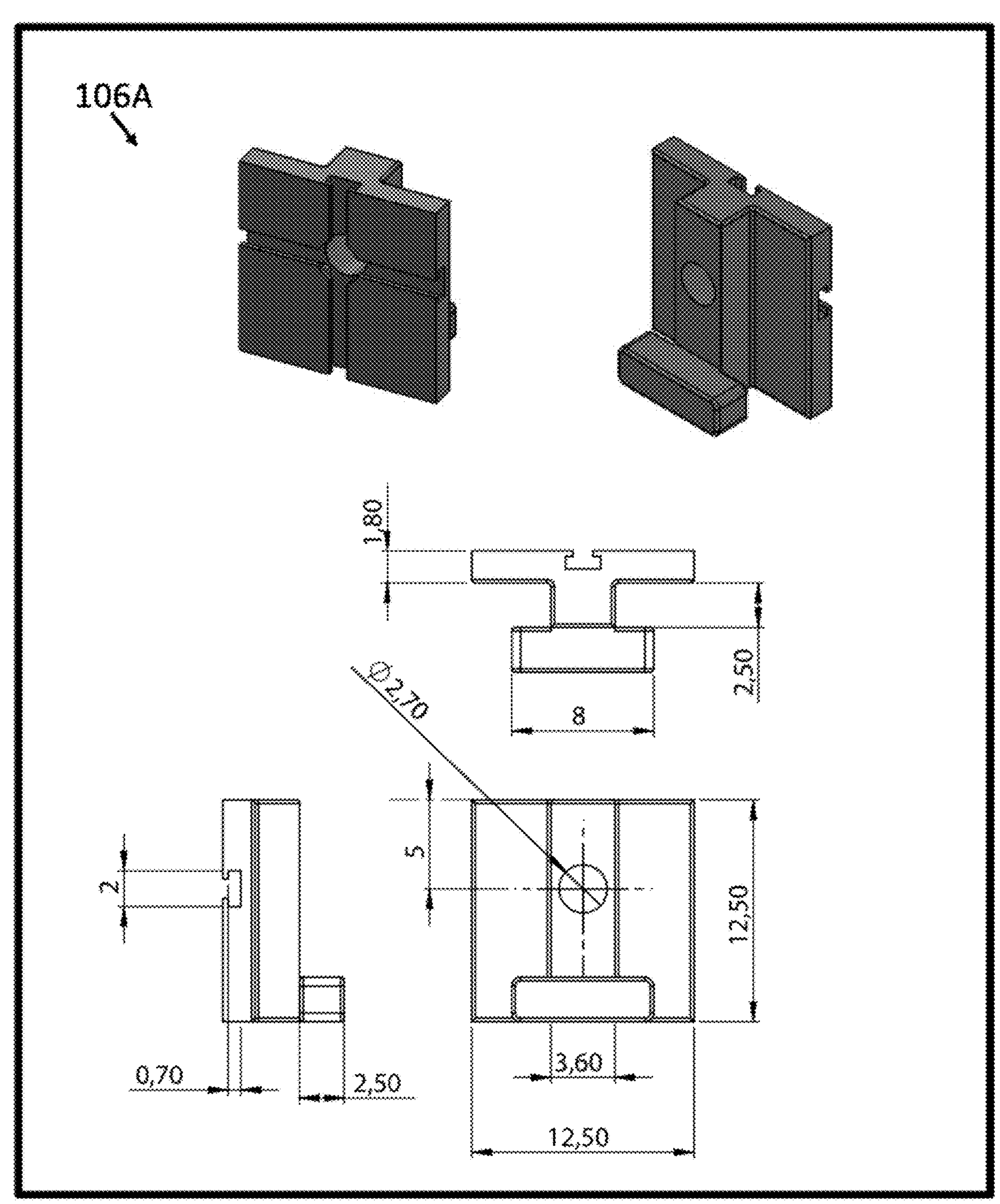
Figures 5F, 5G, 5H, 5I:
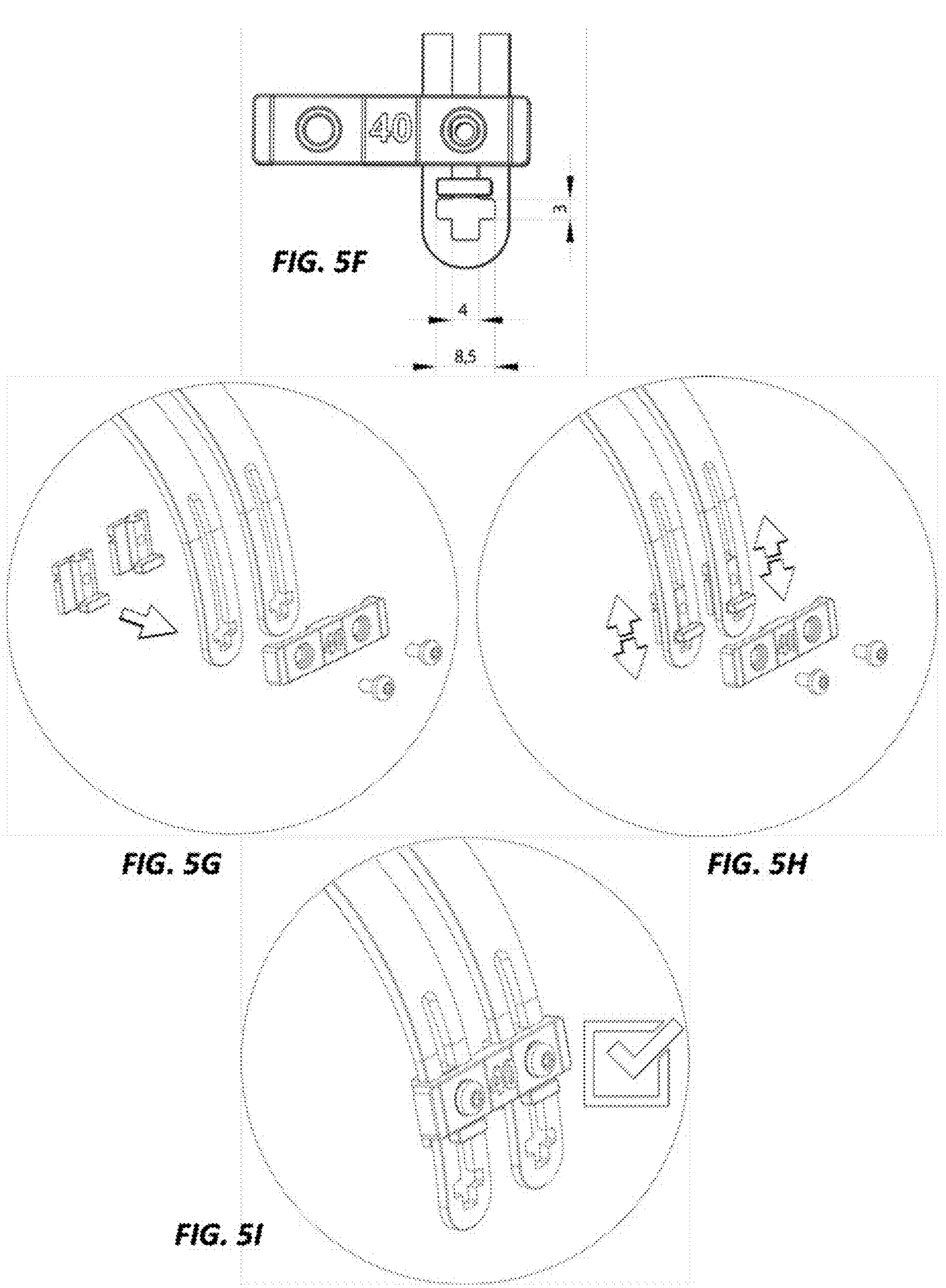
Figures 5J, 5K, 5L, 5M, 5N, 5O:
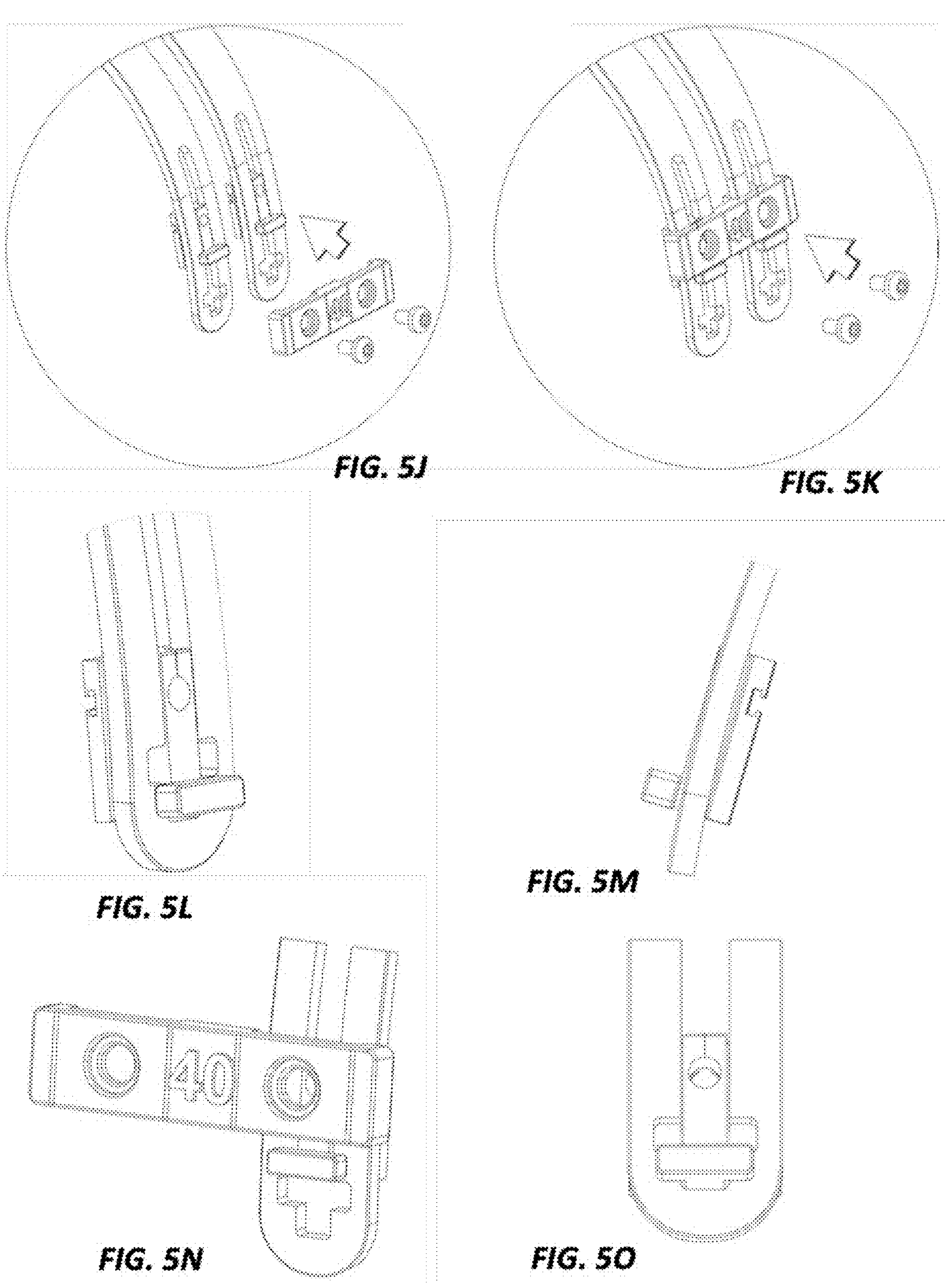

FIGS. 5A-5O show a further embodiment of the invention, where the main stabilization bar 104 includes a T-shape slot. The slider-element 106A further includes a spoiler block 500 configured to limit a range of travel for the slider-element 106A within the stabilization bar T-shape slot, where the screw/fastener and slider element assembly 106 are moveably engaged with the T-shape slot or the linear shape slot (see FIGS. 5B-5O).

Figure 6A:
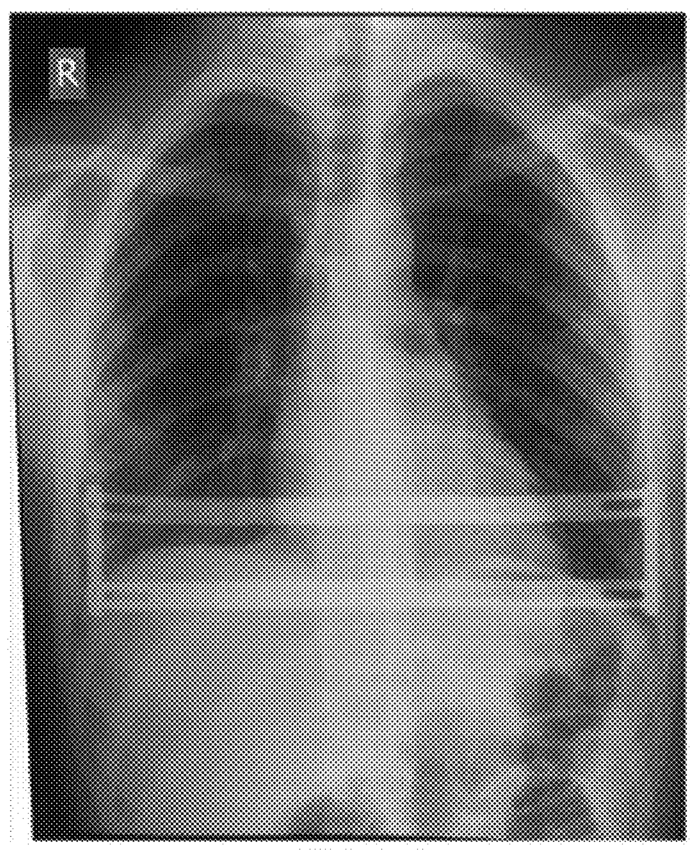
FIGS. 6A-6C show x-ray images of the different embodiments of the flail chest stabilization device implemented to patients, according to the current invention.
Figure 6B:
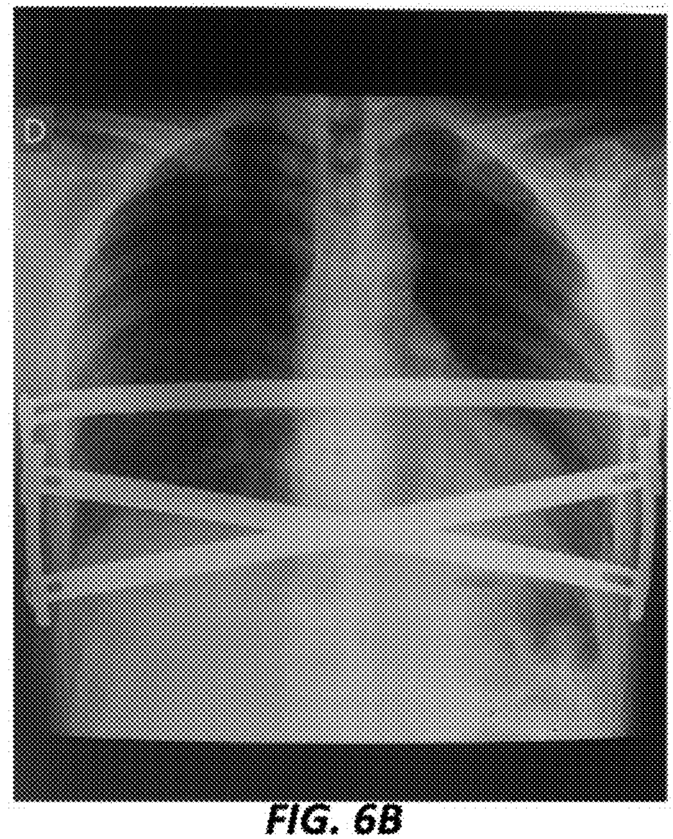
Figure 6C:
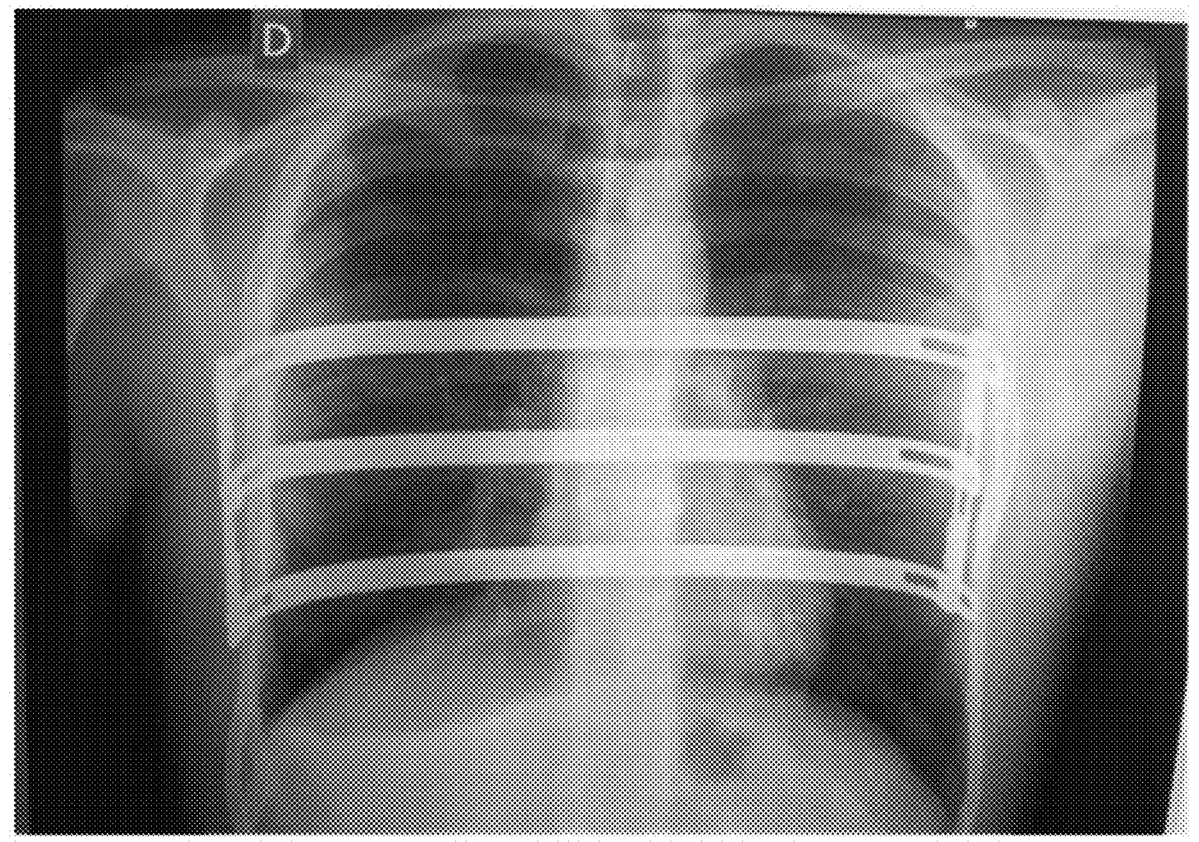
Figure 7:
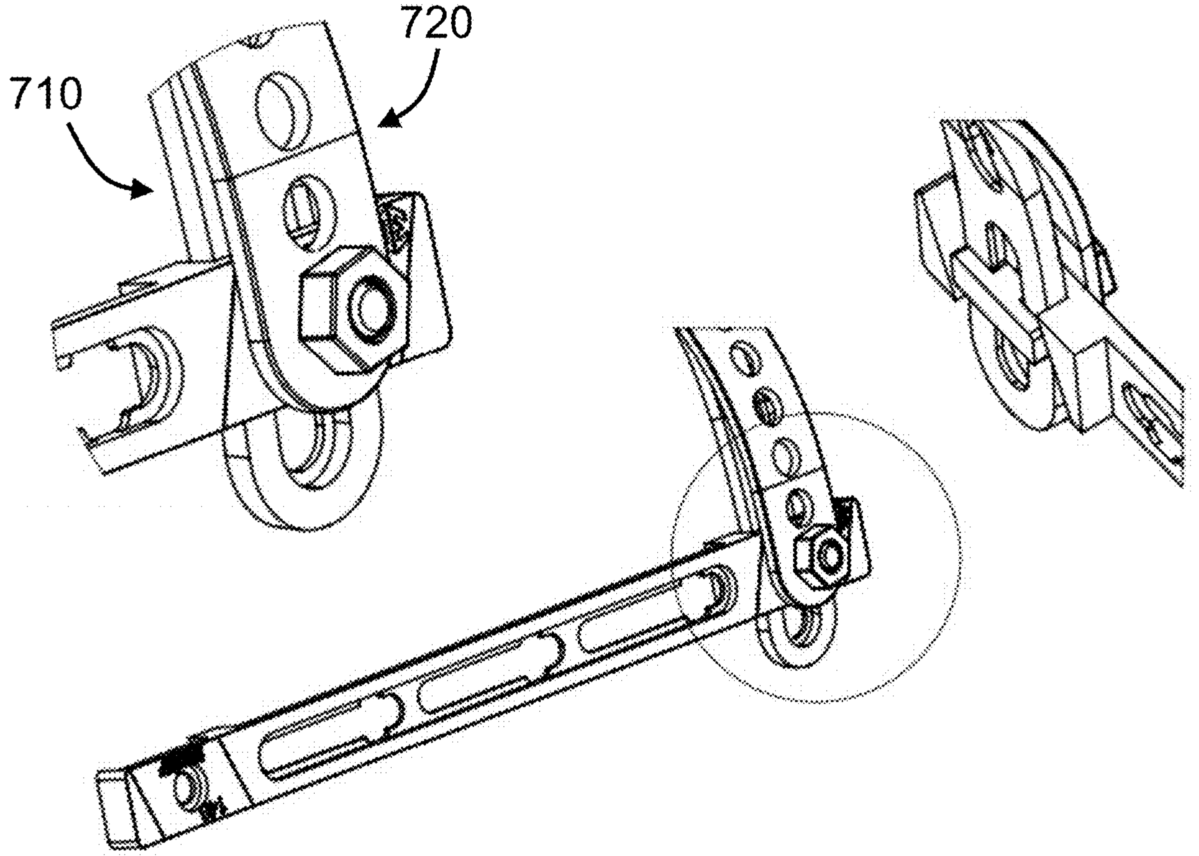
FIG. 7 shows according to an exemplary embodiment of the invention a situation with a double bar 710 and 720 as main stabilization bars.
Figure 8:
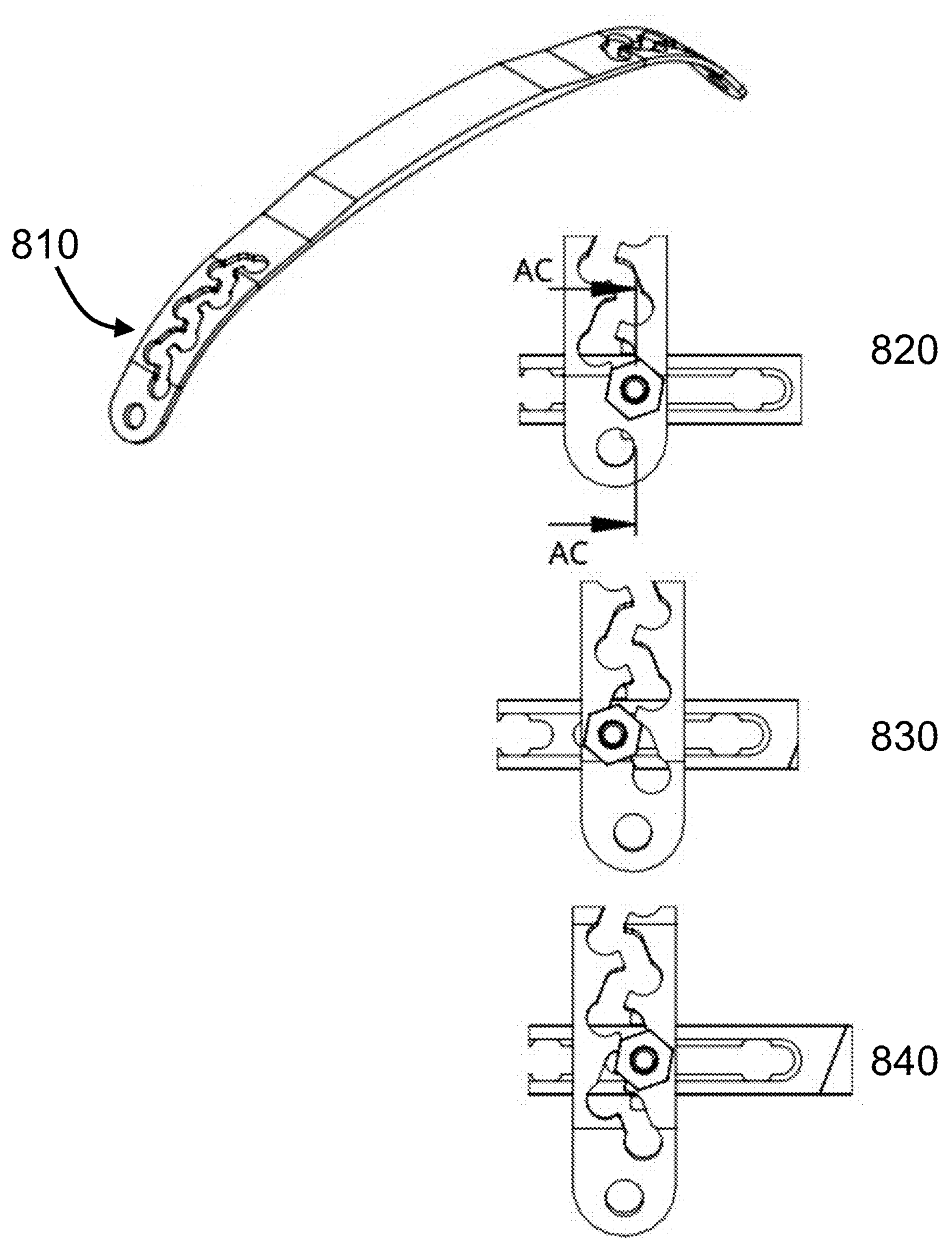
FIG. 8 shows according to an exemplary embodiment of the invention a main stabilization bar or any bar with a wiggly slotted opening 810 and how different positions in the wiggly slotted opening 810 could be used for fastening the bar as indicated in 820, 830 and 840.
Figure 9:
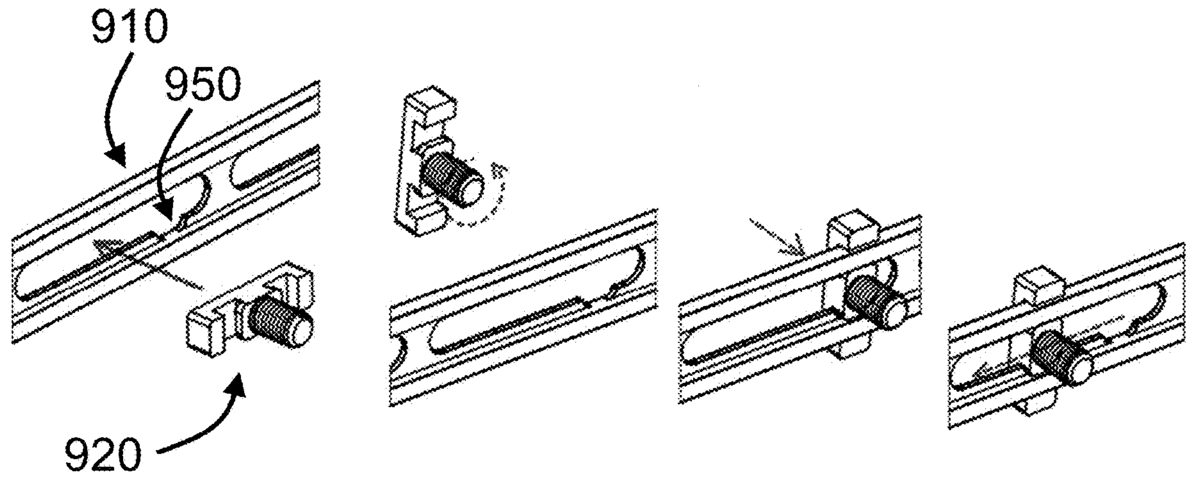
FIG. 9 shows according to an exemplary embodiment of the invention a variation on a fastener and slider-element connector assembly where slider-element 910 and fastener 920, 320 or 940 could be used together. The key aspect of these fasteners is that they are inserted to the slider-element with a turn of the fastener into slot 950 (e.g. by a 90 degree turn maneuver).
Figure 9:
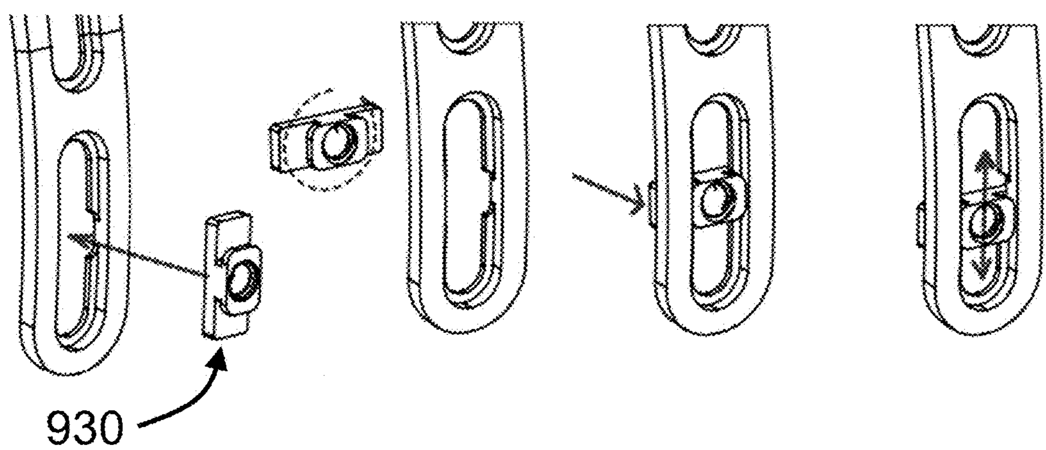
Figure 9:
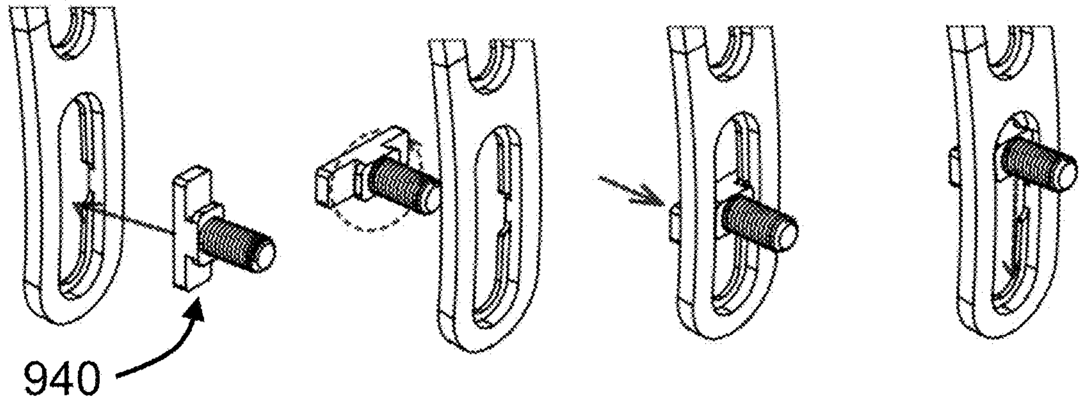

In yet another aspect of the invention, the flail chest stabilization device implants to a patient's body without connecting to a muscle, a rib or any surrounding tissue. FIGS. 6A-6C show x-ray images of the different embodiments of the flail chest stabilization device 100 implemented to patients.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, one embodiment provides a structural implant that will reshape and or stabilize the surgical remodeling of complex congenital chest wall deformities such as Currarino Syndrome, Pectus Arquatum, Poland Syndrome, Pectus Excavatum and Pectus Carinatum in all its variants and Jeune Syndrome and any variant of congenital or acquired chest wall deformity. A further embodiment provides a structural implant that will stabilize and or replace the chest wall after the surgical reconstruction and or stabilization following massive resection of chest wall sections due to chest wall tumors.

What is claimed is:

1. A flail chest stabilization system, comprising:

a) a pair of lateral bridges;

b) a pair of main stabilization bars;

c) a fastener and slider-element connector assembly;

d) a slider introducer tool, wherein the slider introducer tool positions the slider-element connector, wherein the main stabilization bars are connected by the fastener and slider-element connector assembly to the pair of lateral bridges, wherein the stabilization bars are in a parallel configuration or crossed configuration; and e) a middle stabilization bar connected to the pair of lateral bridges, wherein the middle stabilization bar is connected to the pair of lateral bridges by lateral secondary mini-bridges, wherein the lateral secondary mini-bridges are connected to the pair of lateral bridges, and wherein the middle stabilization bar is connected to the lateral secondary mini-bridges.

2. The flail chest stabilization system of claim 1, wherein each of the main stabilization bars has a thickness which is thicker in a center region relative to an end region of the respective main stabilization bar, wherein the thickness decreases in a continuous fashion region toward the end region, and wherein the thicker center region imparts a central stabilization force that is greater than an end stabilization force.

3. The flail chest stabilization system of claim 1, wherein each of the main stabilization bars comprise a T-shape slot, a linear shape slot, a slidable slot or a wiggly shape slot at each end regions, wherein the fastener and slider-element connector assembly is moveably engaged with the T-shape slot, the linear shape slot, the slidable slot or the wiggly shape slot.

4. The flail chest stabilization system of claim 3, wherein the fastener and slider-element connector assembly further comprises a spoiler block configured to limit a range of travel for the slider-element connector assembly within the T-shape slot, the linear shape slot, the slidable slot or the wiggly shape slot.

5. The flail chest stabilization system of claim 3, wherein the middle stabilization bar comprises a single thickness from end to end, wherein the middle stabilization bar comprises a plurality multiple threaded holes, or the T-shape slot, the linear shape slot, the slidable slot or the wiggly shape slot on each said end.

6. The flail chest stabilization system of claim 3, wherein the middle stabilization bar is configured to impart a force that goes from front to back of a rib cage, wherein the imparted force flattens asymmetric deformities or stabilizes fractured bones.

7. The flail chest stabilization system of claim 1, wherein the flail chest stabilization device is capable of being implanted to a patient's body without attaching to a rib.

8. The flail chest stabilization system of claim 1, wherein the lateral bridges comprise a flat or curved profile.

9. The flail chest stabilization system of claim 8, further comprising a superior parallel stabilization bar, wherein the pair of main stabilization bars are connected to the pair of lateral bridges with a curved profile in the crossed configuration, or wherein the superior parallel stabilizer bar is connected to the pair of lateral bridges with a flat profile, and wherein the pair of lateral bridges with a flat profile are further connected to the main stabilization bars.

10. The flail chest stabilization system of claim 1, wherein the slider introducer tool is positioned under the main stabilization bar during a surgical procedure.

11. A flail chest stabilization device, comprising:

a) a pair of lateral bridges;

b) a pair of main stabilization bars each having a thickness and two end regions, wherein each of the main stabilization bars has a thickness which is thicker in a center region relative to an end region of the respective main stabilization bar, wherein each thickness decreases in a continuous fashion towards the end region, and wherein the thicker center region imparts a central stabilization force that is greater than an end stabilization force; and c) a fastener and slider-element connector assembly; and d) a middle stabilization bar connected to the pair of lateral bridges, wherein the middle stabilization bar is configured to provide antero-posterior stabilization, wherein the middle stabilization bar is connected to the pair of lateral bridges by lateral secondary mini-bridges, wherein the lateral secondary mini-bridges are connected to the pair of lateral bridges, and wherein the middle stabilization bar is connected to the lateral secondary mini-bridges.

* * * * *